(12) United States Patent
Solosko et al.

(10) Patent No.: US 7,139,615 B2
(45) Date of Patent: Nov. 21, 2006

(54) SINGLE SEPARABLE ELECTRODE AND SELF-CONTAINED PAD VIABILITY TESTER

(75) Inventors: Thomas Solosko, Issaquah, WA (US); Gregory D. Brink, Bainbridge Island, WA (US); Joel Rosenwelg, Marlborough, MA (US); Fred Borgenicht, Dover, MA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 424 days.

(21) Appl. No.: 09/984,789

(22) Filed: Oct. 31, 2001

(65) Prior Publication Data

US 2003/0083729 A1    May 1, 2003

(51) Int. Cl.
*A61N 1/04* (2006.01)

(52) U.S. Cl. .................................................. 607/142
(58) Field of Classification Search ................ 600/382, 600/386; 607/142; 206/459.1, 438
See application file for complete search history.

(56) References Cited

U.S. PATENT DOCUMENTS

| | | | | |
|---|---|---|---|---|
| 5,817,151 A | * | 10/1998 | Olson et al. ................. | 607/142 |
| 6,076,002 A | * | 6/2000 | Cartmell et al. ............ | 600/372 |
| 2003/0055478 A1 | * | 3/2003 | Lyster et al. ................ | 607/142 |

* cited by examiner

*Primary Examiner*—Robert E. Pezzuto
*Assistant Examiner*—Frances P. Oropeza

(57) ABSTRACT

A single separable electrode that includes a plurality of separable electrically connected electrode sections.

4 Claims, 6 Drawing Sheets

SINGLE SEPARABLE ELECTRODE AND SELF-CONTAINED PAD VIABILITY TESTER

FIELD OF THE INVENTION

The present invention relates to a single separable electrode that permits verification of functionality of subsections of the electrode sealed within a package without unsealing the package. Also, the present invention relates to a method for determining functionality of components sealed within a package without unsealing the package.

BACKGROUND OF THE INVENTION

Products are sealed in packages for various reasons. These reasons include maintaining sterility of the products, preventing contact of the products with air preventing moisture loss or gain from the product, and for protection during shipping. For any one or more of these reasons, it may be desired to maintain a certain atmosphere within a sealed package. Therefore, opening these packages to determine product viability is not possible since the act of opening the package changes or destroys the desired atmosphere within the package.

To ensure that medical devices in particular are suitable for use, a destruction policy often requires discarding all devices over a certain age. This may be necessary due to the inability to determine the viability of a device inside a sealed package. Such a destruction policy may result in discarding and thereby wasting viable devices.

For example, defibrillation electrode pads may include several electrical connections and a hydrogel that facilitates their operation. The shelf life of electrode pads is determined in part by the length of time it takes for enough water moisture to evaporate out of the hydrogel and escape the pads package. As moisture escapes, the electrical properties of the electrode pads become increasingly compromised.

In one context, where electrode pads are utilized with a defibrillator, a very significant factor includes changes in small and large signal impedance values between a patient's skin and the defibrillator. As the hydrogel dries out, the impedance values increase, making it more difficult to monitor a patient's electrical signals, obtain transthoracic impedance, and deliver energy into the body. Electrical continuity is compromised between the electrode and a patient's skin.

To help ensure that electrode pads will be usable when opened, electrode manufacturers currently print an expiration date on each set of pads. The electrode pads are to be discarded no later than the expiration date. However, the expiration date typically is determined based upon studies of the hydrogel used on the pads, and the amount of water moisture that escapes the package over time under normal as well as strenuous conditions. A safety factor is added to give time for the electrode pads to be shipped from the supplier to an original equipment manufacturer (OEM) and then from the OEM to the customer. This helps to ensure that the electrode pads are always usable, barring any package damage, when removed from the package before the expiration date.

Calculating the expiration date of electrode pads or other components as described above is a conservative method of ensuring quality. However, as a result, the expiration date may arrive before the pads have actually expired. In fact, electrode pads may be usable for much longer than the expiration date, especially if they are kept at room temperature or in a high humidity environment.

While electrode pads or other components may naturally over time become nonfunctional, at other times an electrode package may be damaged in some way. For example, tiny punctures or slits in the package, which may be too small to be seen by the casual observer or with the naked eye, or tears in the metal packaging layer caused by bonding the package, can allow water moisture to escape. Without noticing damage to the electrode pads' package, a customer typically will not replace electrode pads until the expiration date arrives, when in fact the pads may be unusable long before. In addition, an electrode may be bent or compressed inside its sealed package, thereby causing electrical discontinuities such as broken wires or connections.

The above example only represents one particular example of an electrode pad of a particular use. Electrode pads for other uses may be similarly affected. Also, devices other than electrode pads may be affected by age, storage, and package conditions. Furthermore, factors other than humidity can affect the functionality of a device.

SUMMARY OF THE INVENTION

The present invention addresses problems related to ensuring operability of packaged devices. The present invention may be useful with a variety of products affected by a variety of conditions within packaging that contains the products. One advantage of the present invention is that the functionality of a device or component may be measured directly or indirectly while the device or component is still sealed in a package.

As such, the present invention provides a method for determining functionality of a component in a sealed package. At least one parameter including an electrical function parameter of the component is measured while the component is sealed within the package. While the component is sealed within the package it is determined whether the parameter corresponds to an acceptable value at which the component functions and it is indicated whether the parameter corresponds to an acceptable operational value for the component.

The present invention also includes a method for preparing a single patient skin contacting electrode that can be separated into two or more electrodes for use. The method includes removing the electrode from a sealed package and separating the electrode into two or more separate electrodes.

Still further, the present invention provides a skin-contacting electrode that includes a single electrode that is separable into two or more electrodes.

Still other objects and advantages of the present invention will become readily apparent by those skilled in the art from a review of the following detailed description. The detailed description shows and describes preferred embodiments of the present invention, simply by way of illustration of the best mode contemplated of carrying out the present invention. As will be realized, the present invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DETAILED DESCRIPTION OF THE INVENTION

Figure 1A:
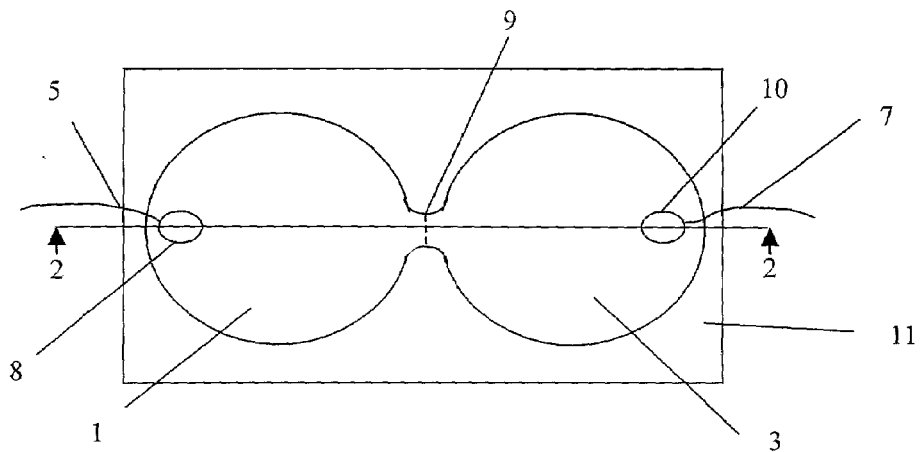
FIG. 1a represents an overhead view of an embodiment of an electrode that may be separated into two electrodes according to the present invention wherein the two electrodes are arranged end-to-end.

As discussed above, storage conditions can affect the functionality of many devices. Temperature, humidity, environment, age, pressure, external forces and/or other factors may be relevant, thereby preventing the package from being opened to determine the viability of the device. When sealed in a package, the functionality of a device typically cannot be known. Even out of a package, it may not be possible or easy to determine the operational status of a device. For example, it may be difficult to see an electrical discontinuity particularly in a situation where the pad is urgently required and/or any testing equipment is not present. Therefore, it may be desirable to have a way to measure the functionality of a device, such as an electrode, while the device is still sealed in a package.

The present invention addresses problems associated with determining whether devices sealed within a package are functional. In the context of electrode pads, the present invention also provides a method and structure for determining the operability of electrode pads while still packaged, regardless of the cause. Although electrode pads are specifically mentioned here, the present invention may be applied to devices other than electrode pads and to conditions other than electrical discontinuities that can affect operability of any device.

With respect to determining electrical functionality of electrode pads, preconnected electrodes, electrodes operatively connected electrically to fit a defibrillator before an emergency occurs, offer the possibility of testing the continuity of the electrical path from the defibrillator, through both electrode pads and back to the defibrillator. Several electrode continuity-testing schemes are possible.

A significant aspect of existing schemes involves the manner in which electrical contact is made between the two or more electrodes. According to one scheme, an electrical conductor is placed in contact with the hydrogel of both electrodes. The test current goes through the lead wire of a first electrode, into the conductive layer, through the gel of the first electrode and then through the gel of a second electrode, into its conductive layer, through its lead wires and back to the device.

The above-described methods have one thing in common- the current is forced to travel through the hydrogel of the electrode pads. While this may help to ensure that the gel and the connections continue to conduct electricity, the present invention can provide an entirely different method of testing electrode pads for fitness of use without testing through the hydrogel layers.

In the context of testing electrodes, the present invention permits performance of a continuity test without forcing current to travel through the gel of either electrode. This may be accomplished by directing the electrical path from the defibrillator, through a single separable electrode and back to the defibrillator. According to one embodiment, the conductive layer of the single, separable electrode, which may comprise tin, graphite, and/or other conductive materials, may span an area equal to two or more separate electrodes, thus remaining operatively connected until the electrodes are removed from their package. As discussed below, an electrode according to the present invention can span an area equal to a plurality of subelectrodes that may be separated when utilized. Because current flow takes the least resistant path to ground, and because a hydrogel has a greater resistance to current flow than the conductive layer, the single conductive layer forces the current to travel from the defibrillator, through the conductive layer of a first side of the single separable electrode and back to the defibrillator without ever traveling through the electrode gels. This therefore tests all of the electrical connections in the path without altering the hydrogel in any way.

The single separable electrode pad may be accomplished in a number of ways. According to one embodiment, the single electrode may be manufactured with one or more narrow strips of the conductive layer joining the two or more sections that will later be separated into distinct pads. In this embodiment, the die used to cut the conductive layer would not completely separate the sections. Rather, the die would leave one or more narrow conductive ties between the two otherwise separate electrode sections. The gel and dielectric layers would continue to be individually cut and placed on their separate conductive halves. When completed, the single separable electrode would be placed on a common release liner, or separate liners, folded and placed in a package.

The present invention also includes a single separable electrode with sections that may be electrically connected together. When electrically connected, the electrode sections may be considered to be one electrode that includes a plurality of subelectrodes. Along these lines, the present invention can include a plurality of joined electrodes. The joined electrodes may be separated. To provide both electrical connection and separability, the electrical connection(s) may be separable. The electrical connection may be provided by a continuous electrically conductive layer extending among the sections. The electrically conductive layer can permit continuity testing of the entire electrode including the subelectrodes. A separable dielectric layer may also extend among the electrodes. In some embodiments, the dielectric layer may not extend among the electrodes.

When the electrodes are ready for use, subelectrodes may be separated from each other. The separation may be carried out by cutting or otherwise severing the connection between adjacent electrodes. Some embodiments may include a perforation of the connection between adjacent electrodes to facilitate the separation.

In some embodiments, the electrode sections may be rolled in a roll. This is particularly applicable where the electrodes are connected end-to-end to form an elongated line of electrode sections. Rolling the sections can facilitate their storage and transportation since they will take up a reduced space. In rolling the electrodes, the sections may be rolled about a mandrel.

Figure 1B:
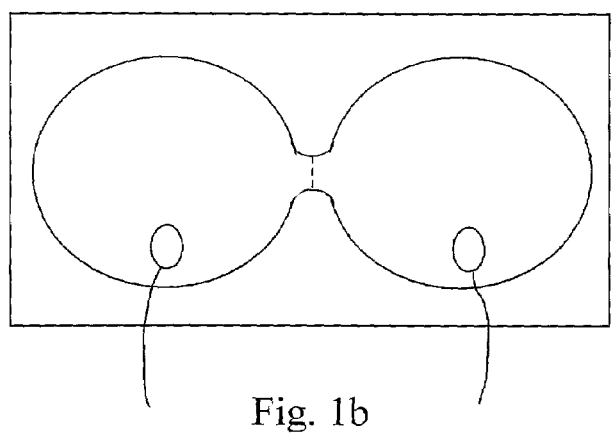
FIG. 1b represents an overhead view of an embodiment of an electrode that may be separated into two electrodes according to the present invention wherein the two electrodes are arranged side-by-side.

FIG. 1 illustrates an example of an embodiment of a single separable electrode where two electrode sections are connected with a built in electrical short for testing. Along these lines, FIG. 1 illustrates two electrode pad sections 1 and 3. Leads 5 and 7 extend from sections 1 and 3. The leads may be attached to the electrode with electrode attachment elements 8 and 10. A perforated connection 9 between electrode pads 1 and 3 results from the incomplete separation of the electrode pad sections when cut from a sheet or roll of material.

When a user removes the pads from a liner 11, the perforation may be severed. Alternatively, the connection may be broken by tearing the conductive strip joining the conductive layers of the two sections. Also, the connection may be cut. Since the gel and dielectric, or foam, are separate pieces, no tearing or cutting through gel or dielectric is required. According to another embodiment, the conductive strip connecting the electrode sections may by tied into the package, clamped or bonded to the inside of the package. In this embodiment, the conductive strip between the two sections tears when the user removes the electrode from its package. According to another embodiment, the dielectric extends between the electrodes. The conductive strip and dielectric are both torn or cut upon removal from the package to separate the single electrode into two or more electrodes.

Figure 2:
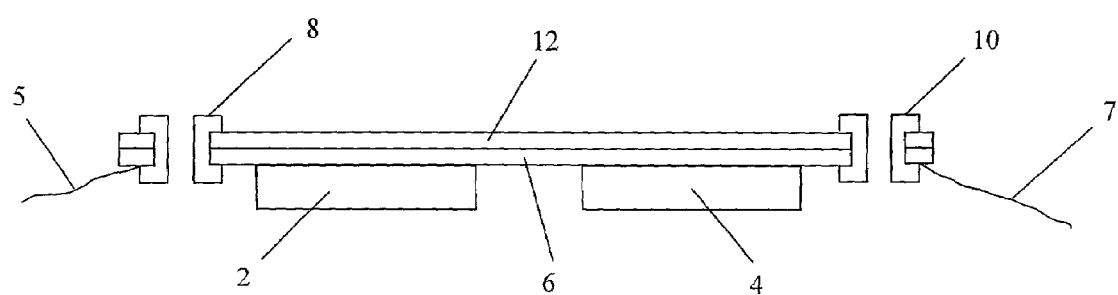
FIG. 2 represents a cross-sectional view of an embodiment of an electrode according to the present invention.

FIG. 2 illustrates a cross-sectional view of one embodiment of an electrode as shown in FIG. 1 that may be separated into two electrodes. The electrode shown in FIG. 2 includes two regions of hydrogel 2 and 4 attached to a conductive layer 6. The conductive layer typically is continuous so as to extend among all connected electrode sections, thereby providing electrical continuity among the sections. The electrically conductive layer may be formed of any suitable electrically conducting material. According to one example, the electrically conducting layer includes tin.

Figure 3:
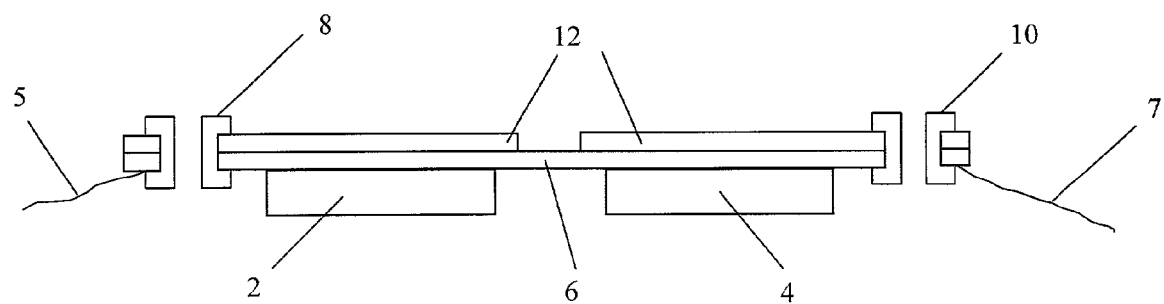
FIG. 3 represents a cross-sectional view of another embodiment of an electrode according to the present invention.

A dielectric layer 12 may be arranged on the electrically conducting layer. As shown in FIG. 2, the dielectric layer may extend between the conductors as the electrically conducting layer. Alternatively, only the electrically conducting layer may extend among the electrode pads, as shown in FIG. 3.

According to another embodiment that permits electrodes to be tested while still sealed in a package, conductive electrode layers of the single separable electrode are cut separately. The cutting may be accomplished with a die or otherwise. Also, any suitable electrically conductive material may be utilized, such as tin. After cutting the electrode conductive layers, they are electrically connected by placing a thin piece of tearable electrically conductive material under each conductive layer before adhering the conductive layers to their dielectric backings. The thin piece of electrically conductive material may also be made of tin or any other suitable electrically conductive material. One example of such a material is a material that does not react with or corrode the conductive layer.

Figure 4:
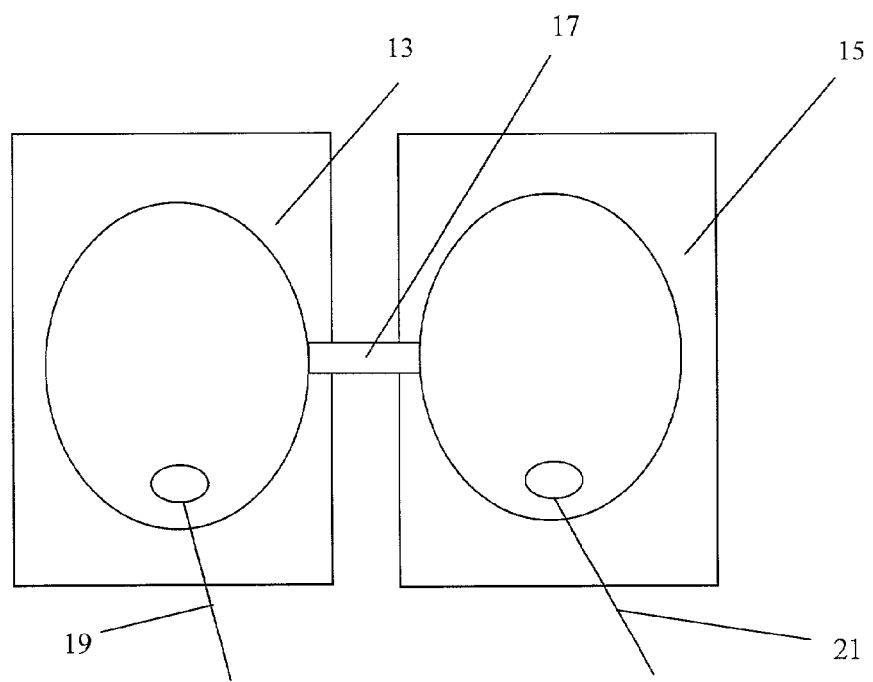
FIG. 4 represents an overhead view of another embodiment of an electrode according to the present invention.

The thin connecting piece of electrically conductive material could electrically connect the two separate conductive electrode layers. It would be bonded to each pad due to the adhesive joining the dielectric layer to the conductive layer. FIG. 4 illustrates an example of such an embodiment. Along these lines, FIG. 4 illustrates an electrode that is separable into two electrodes 13 and 15 with their electrically conductive layers electrically connected by a thin electrically conductive connecting piece 17. Leads 19 and 21 extend from the separable electrode. This conductive connecting strip could be broken in the same manner as mentioned above.

With leads 19 and 21 sealed through the package, the impedance of the single separable electrode can be measured while the electrode is still in the package and before the connection between the subelectrodes is severed. This measurement can be utilized to determine the continuity of the electrical path and the integrity of the electrical connections. To make this measurement, the leadwires may be preconnected to the defibrillator or other device. The device measures the impedance between the leads. A low reading, such as a reading less than about 2 ohms, indicates the electrode and/or the electrical connections are acceptable. On the other hand, a high reading, such as on the order of greater than about 50 ohms, can indicate a bad electrical connection, a crack in the conductive layers and/or a severed lead wire, among other things. In the event that a high reading is obtained, the indicating device would then indicate to the user that the electrodes were not fit for use and needed to be replaced.

The electrically conductive strip could also be removed from underneath the conductive layers of the electrode sections by designing the electrode so that the conductive strip slips out from under the conductive layers before use. This could be accomplished by first arranging a piece of paper, typically a thin piece, on the foam before arranging the conductive layer on the adhesive-backed foam. The conductive strip lies between the paper and the conductive layers.

The paper prevents the conductive strip from sticking to the foam backing. To keep the conductive strip in place, a small amount of very light-force adhesive could be used on its back surface to adhere it gently to the paper. After arranging the conductive strip on the paper, the conductive layer may be arranged on top of the conductive strip. The conductive strip then electrically connects the two conductive layers, but will easily slide out from the electrode sections when they are pulled from the package.

To increase the robustness of the electrical contact with the conductive strips, the strips can be waffled. The waffling will create peaks and valleys in the conductive strips, thereby creating numerous points of contact between the strip and the conductive layer.

Figure 5:
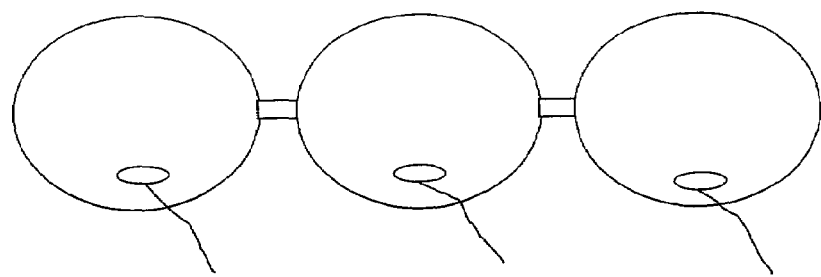
FIG. 5 represents an overhead view of another embodiment of an electrode that may be separated into three electrodes according to the present invention.
Figure 6:
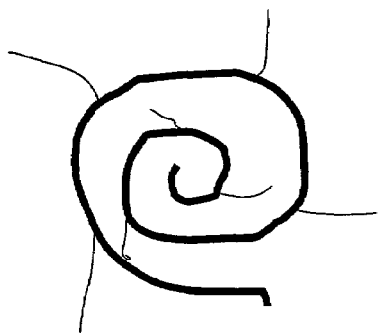
FIG. 6 represents an end view of an embodiment of a roll of electrodes according to the present invention.

According to the present invention, a single separable electrode may be separated into more than two electrodes. For example, FIG. 5 illustrates an embodiment in which the electrode may be separable into three electrodes. Regardless of the number of electrodes that an electrode may be separated into, the electrodes may be packaged as a roll. FIG. 6 illustrates an embodiment of a roll of electrode sections. To facilitate forming a roll from the electrode sections, the electrode sections may be rolled about a mandrel.

Figure 7:
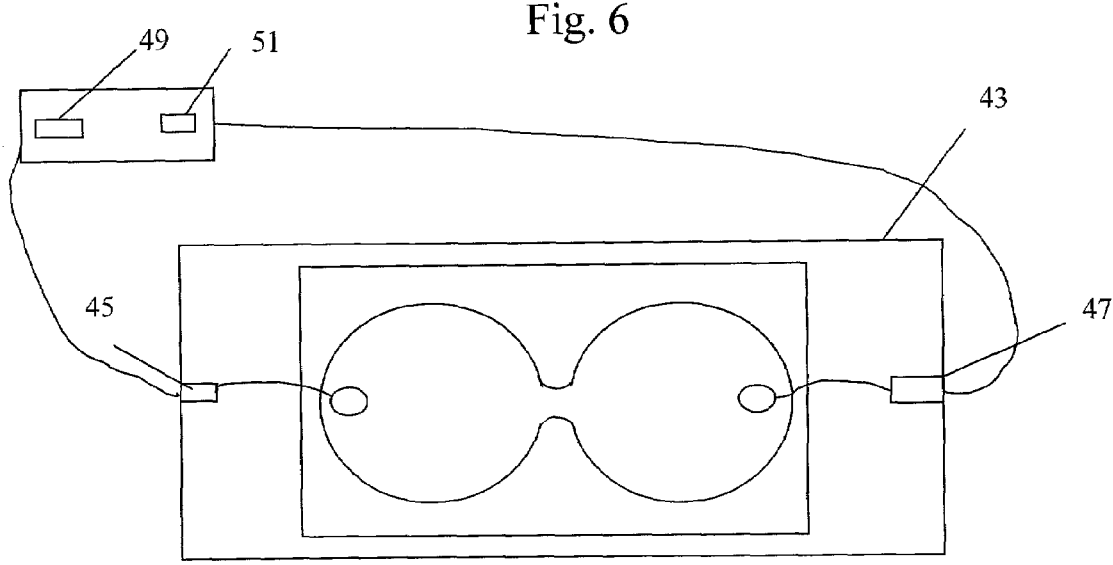
FIG. 7 represents an embodiment of a package that contains an embodiment of an electrode according to the present invention.

FIG. 7 illustrates an embodiment of a sealed package containing an embodiment of an electrode according to the present invention. A package can include one or more package members. The package member(s) could be all or partially rigid. Alternatively, the package member(s) could be flexible. A package could include a mix of both rigid and flexible members. For example, a rigid member could be sealed with a flexible member. According to some embodiments, the package includes a single pouch member.

FIG. 7 illustrates a package member 43. Connectors 45 and 47 may be sealed in the wall of the package as described above. The connectors could be the connectors typically included on the electrode leads. Alternatively, other connectors could be included in the package that the leads are then connected to. An external device may be connected to the connectors to test the electrodes while packaged. The external device may include an indicator 49 for indicating whether or not the electrodes are functional. A user-actuated member 51 may also be included for a user to initiate the process of determining whether electrodes are functional.

To simplify implementation of the present invention, it may be desirable to provide an electrical test of electrode pads or any other device sealed in a package and a simple yes or no indication of viability or functionality in response to user inquiry without opening the sealed package. For example, electrodes or other devices in the package could be operatively connected to a power source. The power source could be within the package or external to the package. If external to the package, the power source could be operatively connected to the electrodes for testing. Along these lines, connectors within the package wall could be attached to the leads from the electrodes. If a user desires to test the electrodes, the power source could be operatively connected to the electrodes. Alternatively, prior to use, the electrodes could always be attached to the power source.

The present invention provides a new way to test electrode connections without testing the gel. In other words, the present invention does not need to run a current through the hydrogel of an electrode pad. The present invention overcomes problems associated with methods and structures for testing operability of electrode pads and/or provides a method and apparatus for monitoring conditions within a package. While the present invention may be useful with any component, as described herein, it was first developed for use with electrode pads.

In a broadest sense, the present invention concerns determining the function of electric components or devices, such as a patient skin-contacting electrode, when still sealed in a package. Along these lines, the present invention includes a package that may include at least one package portion that at least one component or device is sealed within. At least one element permits the determination of at least one electrical function parameter of the at least one component. The at least one element may or may not be sealed within the package. At least one indicator indicates the at least one electrical parameter of the at least one component, thereby permitting the functionality of the at least one component within the sealed package to be determined. Alternatively, the at least one indicator indicates the functionality of the at least one component. The indicator(s) may or may not be sealed within the package.

With electrodes, a sealed package may include at least one connector within the wall of the package. One or more leads may be operatively connected to the electrodes and to the connector(s). A device external to the package may also be operatively connected to the connector. The external device may include a defibrillator, electroencephalograph, cardiac pacing or cardioverting device, electrocardiograph or other device that the electrodes are to be utilized with. Alternatively, another device could be attached to the connector for the purposes of determining one or more electrical functioning parameters.

Whether or not the components or devices sealed in the package are electrodes, measuring at least one electrical functional component can include supplying current to the components. The current flow may be initiated by a user, such as by pressing a button or taking other action to close a circuit. Alternatively, the external device could automatically initiate current flow. In such embodiments, the current flow could be periodically initiated. In some embodiments, a power source could be enclosed within the sealed package to provide current flow to the components.

A processor or other element can interpret current flow parameters through the components. The processor or other element could be included in the external device. At least one indicator can indicate the functionality of the device or the characteristics of the current flow. The indicator could be sealed within the package.

To permit the present invention to help determine the operability of components while still sealed in their packages, the indicator may be visible from outside the sealed package. This does not necessitate the indicator being arranged within the package. In fact, the indicator could lie outside the package and be operatively connected to elements within the package. In such an embodiment, the indicator would be visible from outside the sealed package.

In addition to its location, the nature of the indicator may also change. Functionality or non-functionality reading produced by the indicator(s) may be displayed to a user in a variety of manners, depending upon the embodiment. The indicator in embodiments that include a sensor could include a meter or display, such as any light-producing element. One embodiment can display to the user either a "good/not good" indication. Another embodiment can make the condition of the component clearly visible to the user. An objective of the present invention is to alert a user when electrode pads or any other device are no longer functional. According to some embodiments of the present invention the determining means can be considered the same as the indicating means.

Where the indicator(s) is located within the sealed package, the package may include at least one transparent portion to permit the indicator(s) to be viewed. One inexpensive embodiment of the present invention includes a two-piece package having one transparent portion. According to one embodiment, the package can be one-half metal foil. The other half can be clear or transparent. For example, the clear half can be a clear non-foil laminate. One example of such a laminate is an Aclar laminate, available from Honeywell. The clear or transparent portion may also be formed from Topas®, which is produced by Ticona, or partially metallic clear film like the anti-static film used to package static-sensitive semiconductor components. The clear or transparent package portion can permit a user to view any elements of the invention inside the package.

Embodiments of the present invention that determine at least one electrical parameter of a component in a sealed package can supply a current to the components. The parameter measured can vary. Examples of parameters include current flow, voltage drop through a component, and/or impedance of a component. In some cases, the present invention can include generating an alert when electrode pads are no longer functional and/or need replacing.

Figure 8:
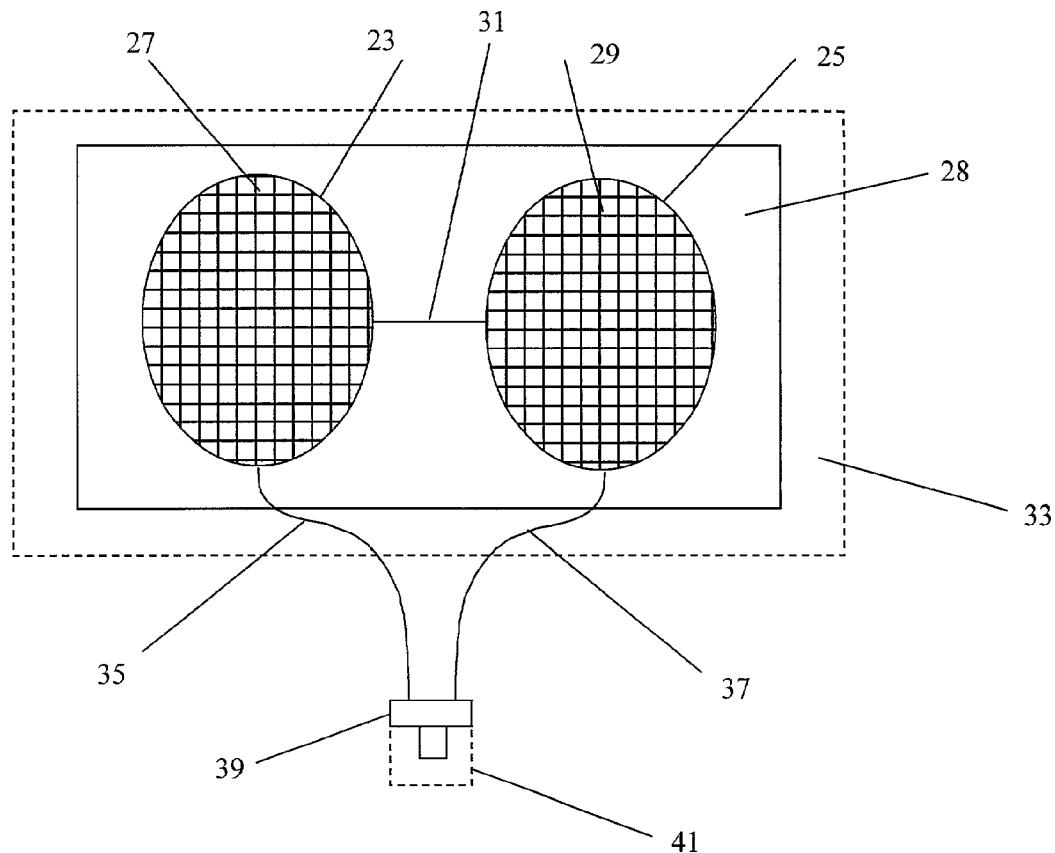
FIG. 8 represents an overhead view of an electrode according to the present invention that includes an embodiment of a self-test function.

FIG. 8 illustrates an embodiment of the present invention that includes elements for a user to initiate an inquiry of electrode pads sealed in a package 33. The embodiment shown in FIG. 8 includes a single separable electrode with two sections, 23 and 25, arranged on a common release liner 28 and connected electrically with a tearable electrically conductive strip 31. Each pad includes a conductive mesh 27 and 29. A conductor 31 connects the pads. A lead 35 and 37 extends from each pad. The leads are attached to a pad connector 39. An end plug 41 contains circuitry that permits the user to initiate an inquiry or permits other elements to be attached to permit the inquiry to be made.

Regardless of where the power source is arranged or how it is operatively connected to the electrodes or other device, the electrodes or other device and power source can be part of a circuit that is only closed in response to user input. An indicator would be part of this circuit. The indicator would indicate that the electrodes or other device are in an acceptable state if the indicator receives sufficient current. The indicator could also produce a signal if the pads are not viable. In some cases, the indicator would only indicate pads in a functional state. Any indicator could be utilized, such as one or more LED's, LCD displays, lights, meters, or other devices. Also, parameters other than current flow could trigger the indicator.

Figure 9:
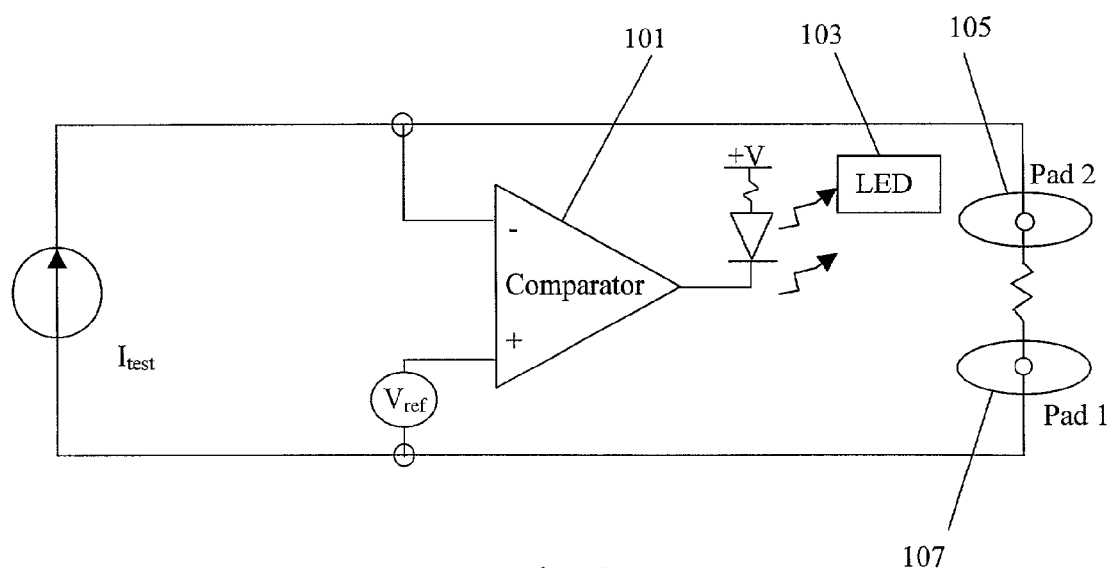
FIG. 9 represents a schematic drawing that illustrates an embodiment of a comparator circuit according to the present invention.

FIG. 9 shows one embodiment of a completely contained pad viability tester according to the present invention that includes circuitry that may be included in the electrode connector and that includes a voltage comparator 101 and an LED 103. The comparator compares a preset threshold voltage against a voltage drop through the electrode pads 105 and 107. If the pads are viable, impedance is low and the comparator will not illuminate the LED.

Figure 10:
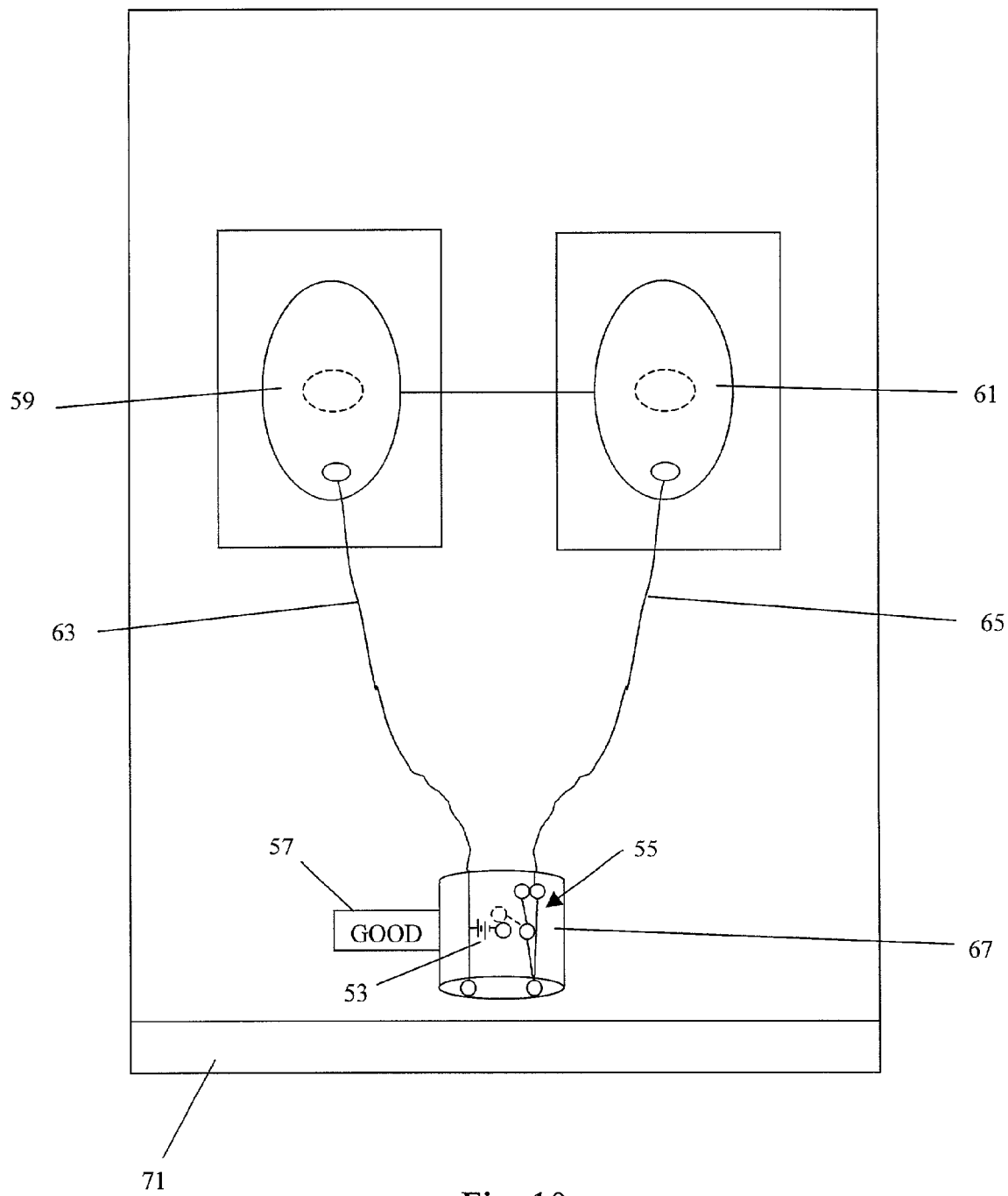
FIG. 10 represents an overhead view of an embodiment of a package according to the present invention.

According to another embodiment, circuitry including a power source, an electrical switch, and an indicator would be enclosed in the sealed package such that a user could close the switch and determine from the indicator whether or not the pads are functional. FIG. 10 illustrates a simple embodiment of this approach. The embodiment shown in FIG. 10 includes a circuit including a power source 53, a switch 55, a liquid crystal window 57, electrode pads 59 and 61, lead wires 63 and 65, and pad connector 67. The power source, switch, and display may be arranged in a connector as shown in FIG. 10 or may be arranged elsewhere in the package. A user would activate the circuit by closing the switch 55. The switch shown in broken lines illustrates the closed position. Closing the switch would permit current to flow through both pads, which are connected via a thin conductor strip as shown in FIG. 10, the lead wires, and the pad connector, thereby verifying the integrity of the entire pad assembly. If sufficient current is able to flow through the circuit, the liquid crystal window becomes clear, permitting a user to view a "GOOD" message 73, that is normally obscured by the liquid crystal.

Figure 11:
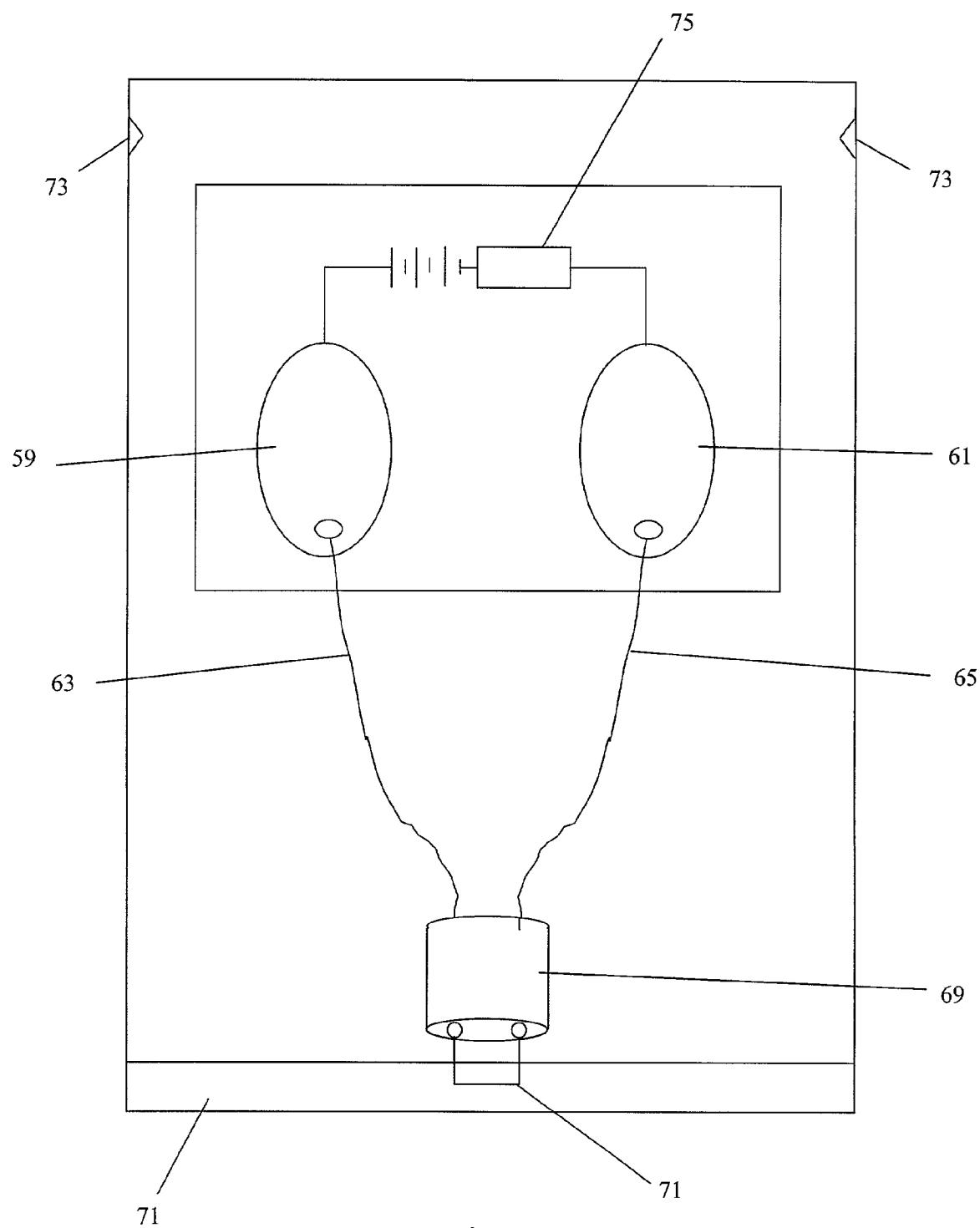
FIG. 11 represents an overhead view of an embodiment of a package according to the present invention.

FIG. 11 illustrates an embodiment of the present invention that includes a pad connector 69 that includes shorting plug 71. The shorting plug is sealed within the package and is removed from the connector as the electrodes are removed from the package. In this embodiment, the plug is partially contained within the package seal as shown in FIG. 11. The package includes a tear, perforation, scoring, or other feature as indicated by elements 73 to facilitate opening the package. A power supply provides power to the circuit. After opening the package, the electrodes are removed and the shorting plug is retained by the package. Alternatively, the shorting plug can be removed as the electrodes are removed from the package. According to this alternative, the electrodes are removed from the package and the shorting plug removed separately after the electrodes are removed from the package. In either of these two embodiments, the power supply may remain on the release liner as the pads are removed from the release liner. If sufficient current is able to flow through the circuit, an indicator 75, such as LED lights or an LCD window, becomes clear to indicate "GOOD" pads as described above.

In the case of electrodes for a defibrillator it is necessary that pads be functional. The present invention provides a package and method for determining whether pads are functional while still sealed in a package. The electrodes may be tested while operatively connected to a device that they are to be utilized with or to another device.

In certain embodiments, the present invention can also permit remote determination of the status of the sealed package and/or the component(s) sealed therein. For example, once the humidity or functional status of the component(s) sealed therein is determined, it could be transmitted via wired or wireless communication means to a location remote from the package. A notification could then be produced that replacement of the component is required. In the case of defibrillator electrode pads, an embodiment with remote notification could alert users about non-functional pads so that they could be replaced to be sure that the defibrillator will function as necessary. This could be particularly important for defibrillators in public places meant to provide defibrillators immediately available on an emergency basis.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. An electrode package including a single separable electrode within the package, wherein the electrode comprises:
    a plurality of separable electrically connected electrode sections; wherein the package further includes
    an indicator operatively connected to the electrode for indicating functionality of the electrode, and wherein the indicator is sealed within the package, the package is flexible and includes at least one transparent portion for making the indicator visible from outside the package.

2. The electrode package of claim 1, wherein the electrode sections are electrically connected to permit continuity testing to be carried out through all electrode sections, said single separable electrode further comprising a separable continuous electrically conductive layer extending among the electrode sections and being separable by at least one of cutting or tearing when removed from the package.

3. The electrode package of claim 1, wherein the sealing creates a seal that contains the electrode and that, upon breaking said seal, leaves the electrode unsealed.

4. The electrode package of claim 1, wherein the sealing creates a seal that contains the electrode and said indicator, the visibility of the indicator being from outside said package without unseating said package.

* * * * *